(12) United States Patent
Stetter et al.

(10) Patent No.: US 6,217,766 B1
(45) Date of Patent: Apr. 17, 2001

(54) SULPHUR REDUCING BACTERIUM AND ITS USE IN BIOLOGICAL DESULPHURIZATION PROCESSES

(75) Inventors: Karl Otto Stetter, Regensburg; Harold Huber, Hausen, both of (DE); Cees Jan Nico Buisman, Harich (NL); Henk Dijkman, Ijlst (NL); Johannes Pieter Krol, Sneek (NL)

(73) Assignee: Biostar Development C.V., Balk (NL)

( * ) Notice: Subject to any disclaimer, the term of this patent is extended or adjusted under 35 U.S.C. 154(b) by 0 days.

(21) Appl. No.: 09/230,081
(22) PCT Filed: Jul. 16, 1997
(86) PCT No.: PCT/NL97/00418
§ 371 Date: Mar. 24, 1999
§ 102(e) Date: Mar. 24, 1999
(87) PCT Pub. No.: WO98/02524
PCT Pub. Date: Jan. 22, 1998

(30) Foreign Application Priority Data

Jul. 16, 1996 (EP) .................................. 96202023

(51) Int. Cl.$^7$ ................. C02F 3/30; C12N 1/12
(52) U.S. Cl. ........... 210/605; 210/612; 210/621; 210/630; 435/252.1
(58) Field of Search ................. 210/601, 605, 210/612, 621, 630; 435/252.1

(56) References Cited

U.S. PATENT DOCUMENTS 4,124,501 * 11/1978 Yen .
4,200,523 * 4/1980 Balmat .
4,584,271 * 4/1986 Stern .
4,614,588 * 9/1986 Li .
4,839,052 * 6/1989 Maree .
4,966,704 * 10/1990 Sarner .
5,496,729 * 3/1996 Monticello .
5,518,619 * 5/1996 Busiman .
5,587,079 * 12/1996 Rowley .
5,637,220 * 6/1997 Buisman .
5,891,408 * 4/1999 Buisman .

FOREIGN PATENT DOCUMENTS

WO 93/24416  12/1993 (WO) .

OTHER PUBLICATIONS

R. K. Nilsen et al., "Desulfotomaculum Thermocisternum sp. nov., a Sulfate Reducer Isolated From Hot North Sea Oil Reservoir", Int. J. Stst. Bacteriol. Apr. 1996, vol. 46, pp. 397–402.

* cited by examiner

Primary Examiner—Chester T. Barry
(74) Attorney, Agent, or Firm—Young & Thompson

(57) ABSTRACT

A new sulfur-reducing bacterium denoted as KT7 is described. It is a low-GC Gram-positive bacterium related to the genus Desulfotomaculum, capable of reducing sulfite and sulfate to sulfide, having an optimum growth at a temperature between 48 and 70° C. at a pH of between 5 and 9 and at a conductivity of the liquid medium between 0 and 40 mS/cm. It can be used in a process for removing sulfur compounds from water, wherein the sulfur-containing water is subjected to anaerobic treatment with the new sulfur-reducing bacteria, with the addition of an electron donor. The sulfur-containing water can be spent scrubbing liquid from a flue gas desulfurization step.

12 Claims, 1 Drawing Sheet

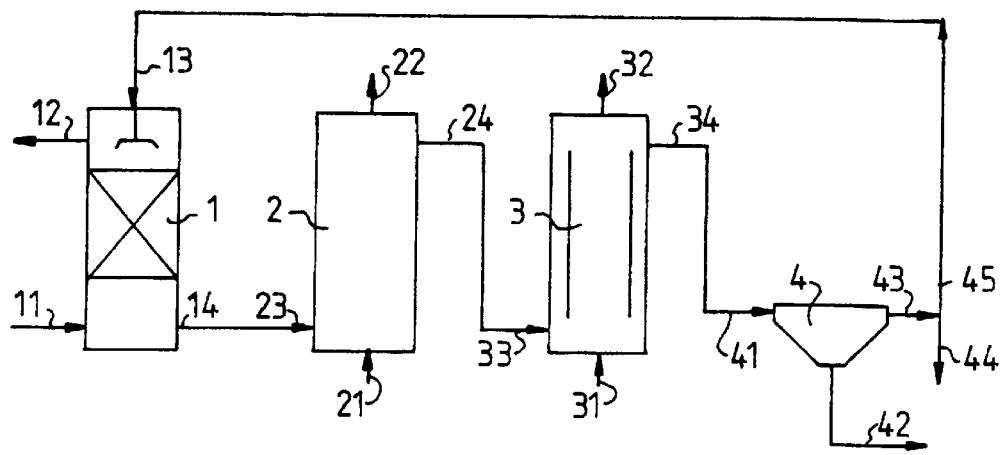
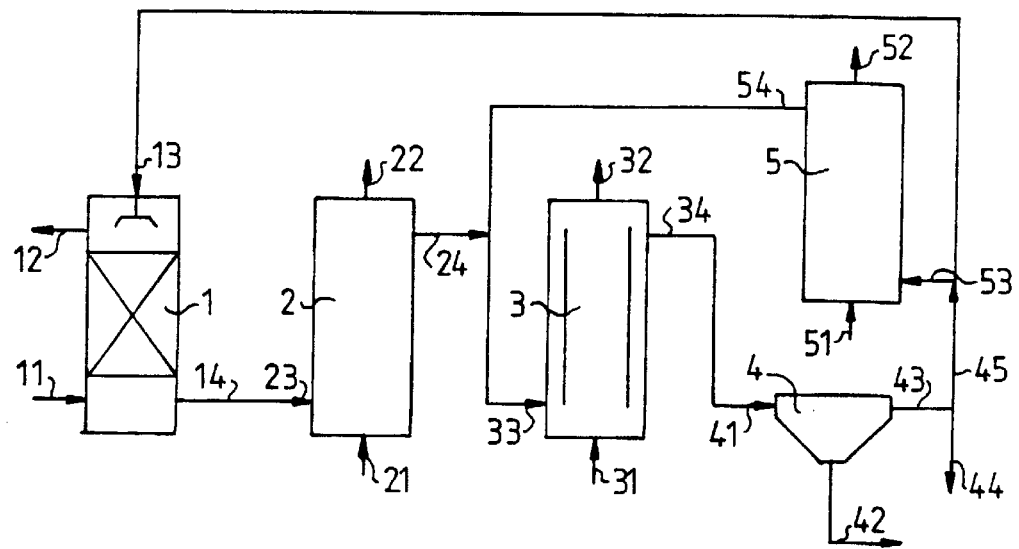

SULPHUR REDUCING BACTERIUM AND ITS USE IN BIOLOGICAL DESULPHURIZATION PROCESSES

CROSS REFERENCE TO RELATED APPLICATION

This is the 35 USC 371 national stage of International application PCT/NL97/00418 filed on Jul. 16, 1997, which designated the United States of America.

FIELD OF THE INVENTION

The invention relates to a new sulphur-reducing bacterium and to a process for removing sulphur compounds from water.

BACKGROUND OF THE INVENTION

The presence of sulphur compounds in water is usually an unacceptable factor. In the case of sulphate, sulphite and thiosulphate, the principal drawbacks are attack on the sewer, acidification, eutrophication, and silting. One type of effluent in which sulphur compounds, in particular sulphite, are a constituent which is difficult to remove is the wash water from flue gas treatment plants. The flue gases from power stations and waste incinerators cause extensive pollution of the environment due to the presence of acidifying sulphur dioxide ($SO_2$). Other types of effluents containing sulphur compounds are those originating from the printing industry, mining industry, and paper, rubber, leather and viscose industry.

The biological treatment of sulphate and sulphite and other sulphur compounds, including scrubbing liquids from flue gas desulphurisation plants, involves reduction in an anaerobic step to give sulphide, which in turn can be biologically oxidised to elementary sulphur. Such processes are known, for example from EP-A-451922, WO-A-92/17410 and WO-A-93/24416.

The advantage of such processes is that only small waste streams remain because the sulphur formed can be re-used. However, the disadvantage is that, especially when the effluent contains little organic matter, electron donors have to be added in order to provide sufficient reduction equivalents for the sulphate reducing bacteria (SRB). The most important electron donors are methanol, ethanol, glucose and other saccharides, organic acids, such as acetic, propionic, butyric and lactic acid, hydrogen and carbon monoxide. The use of these electron donors has the effect of substantially increasing the cost of this method for removal of sulphur from waste streams.

WO-A-92/17410 discloses that sulphur compounds, in particular $SO_2$ can be effectively removed from water by continuous or periodical use of a temperature above 45° C. during the anaerobic treatment, without large amounts of added electron donor being needed, because little or no methane is produced.

According to WO-A-93/24416, the consumption of electron donor can be reduced by selecting a minimum sulphate/sulphite concentration in the anaerobic reactor effluent and/or a minimum sulphide concentration in the reactor and/or by raising the salt concentration. Such measures are more favourable to the SRB than to the methanogenic bacteria, and therefore reduce the total demand for electron donors.

Although such measures have improved the utility of biological desulphur-isation processes, the performance is always limited by the properties of the micro-organisms used. The conventional SRB's used belong to the genera Desulfovibrio, Desulfotomaculum, Desulfomonas, Desulfobulbus, Desulfobacter, Desulfococcus, Desulfonema, Desulfosarcina, Desulfobacterium and Desulfuromonas.

SUMMARY OF THE INVENTION

A new microorganism has been found now which exhibits remarkable and useful properties in the biological reduction of sulphur compounds at high temperatures.

The new microorganism is a bacterium which was isolated from a burning coal heap in Sweden. It can produce high sulphide concentrations from higher oxidised sulphur species such as sulphate and sulphite. High sulphide concentrations, up to 2.5 g/l, can be tolerated by the bacterium without negative consequences for its vitality.

The strain as isolated is denoted as KT7 and consists of short rods, about 0.7–1 μm in diameter and 1–2 μm in length. They stain Gram positive. They are highly motile and several flagellae are visible with electron microscopy. The cells are covered by a protein surface layer. Subunits are regularly arranged with p2 or p4 symmetry.

The bacteria according to the invention fit in the group of the low-GC Gram-positives, and are related to the genus Desulfotomaculuni. They have the characteristics of strain KT7. Strain KT7 has been deposited at the DSMZ in Braunschweig, Germany, on Jun. 19th 1996 with accession number DSM 11017.

The strain K17 is capable of growing in various media. The data of growth on various electron donors and acceptors (concentration 0.1%) after incubation for 3 days are summarised in Table 1 below; the tests were performed under a 80% $N_2$, 20% $CO_2$ atmosphere (2 bar), except for the test with molecular hydrogen which was performed under a 65% $N_2$, 20% $CO_2$ and 15% $H_2$ atmosphere.

TABLE 1

| e-acceptor e-donor | sulphite | sulphate | nitrate |
|---|---|---|---|
| molecular hydrogen | +++ | (+) | (+) |
| formate | ++ | (+) | n.d. |
| acetate | ++ | – | — |
| ethanol | + | (+) | — |
| lactate | +++ | n.d. | (+) |
| isopropanol | + | n.d. | – |
| pyruvate | +++ | n.d. | – |
| fumarate | (+) | n.d. | n.d. |
| citrate | – | n.d. | n.d. |
| D-glucose | (+) | n.d. | n.d. |
| yeast extract | (+) | n.d. | n.d. |

Cell concentrations (cells/ml):
- = no growth
(+) = <$10^7$
n.d. = no data
+ = $1.10^7$ to $3.10^7$
++ = $3.10^7$ to $6.10^7$
+++ = >$6.10^7$ The bacteria according to the invention grow between 35 and 85° C., with considerable growth between 48 and 70° C. The temperature optimum is in the range 50–65° C. with a doubling time of 90 minutes. The pH range for growth is about 5 to 9, with an optimum at 6.5–7.5. The bacteria are active both as free cells and as aggregates.

Strain KT7 is strictly anaerobic. It tolerates up to 25% carbon monoxide in the gas phase. In full scale installations, it is expected that the bacteria can tolerate up to 50% carbon monoxide.

The bacterium according to the invention can be used in various anaerobic processes, especially where sulphate and other sulphur species are reduced to sulphide.

Thus, the invention relates to any process for the biological removal of sulphur compounds from an aqueous solution of dispersion wherein the bacterium as described above is used. The bacterium can be used alone, but also in combination with other, conventional sulphur-reducing microorganisms. An important advantage of the bacterium of the invention is that it can produce high levels of sulphide, about twice as much as conventional sulphur-reducing bacteria, and thus makes the sulphur-reducing process more efficient (higher capacity and/or smaller equipment and/or shorter residence times).

BRIEF DESCRIPTION OF THE DRAWINGS

FIGS. 1 and 2 depict suitable installations for carrying out the invention.

DETAILED DESCRIPTION OF THE INVENTION

A particular embodiment of the process according to the invention is the use in flue gas desulphurisation (BIO-FGD). A flue gas desulphurisation installation can comprise an absorber 1, an anaerobic reactor 2, an aerobic reactor 3, and a sulphur separator 4. In the absorber 1, sulphur dioxide is absorbed from the flue gas byr the scrubbing liquid, which is usually slightly alkaline:

$$NaOH + SO_2 \rightarrow NaHSO_3 \tag{1}$$

A part of the sulphite is oxidised to sulphate as a result of the presence of oxygen in the flue gas:

$$NaHSO_3 + \tfrac{1}{2} O_2 + NaOH \rightarrow Na_2SO_4 + H_2O \tag{1a}$$

In the anaerobic reactor 2, the sulphite and sulphate in the spent scrubbing liquid are reduced to sulphide by means of a hydrogen suppls, in the presence of the bacteria of the invention:

$$NaHSO_3 + 3H_2 \rightarrow NaHS + 3H_2O \tag{2}$$

$$Na_2SO_4 + 4H_2 \rightarrow NaHS + 3H_2O + NaOH \tag{2a}$$

In the aerobic reactor 3, the sulphide is oxidised by sulphide-oxidising bacteria, generally belonging to the colourless sulphur bacteria, such as Thiobacillus, Thiomicrospira, Sulfolobus and Thermothrix. Preferably the oxygen supply in the aerobic reactor is controlled so as to maximise the formation of elemental sulphur rather than sulphate:

$$NaHS + \tfrac{1}{2} O_2 \rightarrow S° + NaOH \tag{3}$$

The alkalinity, used in the absorber unit 1, is recovered in the aerobic stage and no alkaline chemicals are consumed in the overall process:

$$SO_2 + 3H_2 + \tfrac{1}{2} O_2 \rightarrow S° + 3H_2O \tag{1+2+3}$$

After the aerobic reactor 3, the elemental sulphur is decanted or filtered off in a separator 4, and the clarified effluent is reused as a scrubbing liquid.

An installation of the type described above is diagrammatically depicted in FIG. 1: the scrubber 1 has a (flue) gas inlet 11, a gas outlet 12, a liquid inlet 13 and a liquid outlet 14; the anaerobic reactor 2 has an inlet 21 for hydrogen or another electron donor, a gas outlet 22, a liquid inlet 23 connected to 14 and a liquid outlet 24; the aerobic reactor 3 has a controllable air inlet 31, a gas outlet 32, a liquid inlet 33 connected to 24 and a liquid outlet 34; the separator 4 has liquid inlet 41, solid (slurry) outlet 42, and a clarified liquid outlet 43 with return line 45 connected to scrubber inlet 13 and having a surplus liquid outlet 44.

In addition to the components described thus far, the installation may also comprise a second anaerobic reactor 5, shown in FIG. 2, wherein part of the clarified effluent in 45, which still contains sulphate and thiosulphate, is treated with sulphur-reducing bacteria in the presence of hydrogen, and the effluent of the second anaerobic reactor is fed to the aerobic reactor 4. The second anaerobic reactor 5 has an inlet 51 for hydrogen or another electron donor, a gas outlet 52, a liquid inlet 53 connected to 45 and a liquid outlet 54 leading to 33. The optimum flow ratio of clarified effluent (flow in 53: flow in 13) will depend on the composition of the flue gas and on the dimensions of the reactor; it can be e.g. from 10:90 to 30:70, in particular about 15:85.

The second anaerobic reactor 5 may also contain bacteria according to the invention. In a preferred embodiment, sulphite is reduced with free cells in the first anaerobic reactor 2, whereas in the second anaerobic reactor 5 sulphate and thiosulphate are reduced with biomass retention on a carrier; thus, sulphite and sulphate are reduced separately in two anaerobic reactors.

Apart from flue gas scrubbing liquids, various water effluents can be treated using the process of the invention, for example ground water, mining effluent, industrial waste water, for example originating from the printing industry, metallurgy, leather, rubber, viscose and fibre industry, paper industry and polymer industry, and wash water of flue gas treatment plants.

If the bacteria are used in waste water containing organic matter, no additional electron donor may be necessary. Otherwise, an electron donor should be added, which may be hydrogen as illustrated above, but also carbon monoxide and organic compounds such as fatty acids (acetic acid), alcohols (methanol, ethanol), sugars, starches and organic waste. If necessary, nutrient elements are also added in the form of nitrogen, phosphate and trace elements.

The process according to the invention can be used for a wide variety of sulphur compounds: in the first place, the method is particularly suitable for the removal of inorganic sulphate and sulphite. Further possible compounds are other inorganic sulphur compounds such as thiosulphate, tetrathionate, dithionite, elementary sulphur and the like. Organic sulphur compounds, such as alkanesulphonates, dialkyl sulphides, dialkyl disulphides, mercaptans, sulphones, sulphoxides, carbon disulphide and the like can also be removed from water by the process according to the invention.

The sulphide concentration in the effluent of the anaerobic reactor is usually at least 500 mg/l, in particular it can be 800–1000 mg/l, or even higher.

The anaerobic treatment can preferably be carried out at an elevated temperature, in particular at a temperature of 43–75° C., especially at a temperature of 45–70° C. The elevated temperature can be employed continuously, for example when an inexpensive energy source is available, as in the case of hot flue gases and/or a warm wash liquid.

The product from the process according to the invention is, if post-oxidation is applied, elementary sulphur, which can be separated off simply from water, for example by settling, filtration, centrifuging or flotation, and can be re-used, for example for the production of sulphuric acid.

EXAMPLES

Example 1

A reactor of 6.5 l was run under anaerobic conditions at 50° C., pH 7.0 and conductivity of 20–25 mS/cm. The reactor was inoculated with 500 ml of crushed granular sludge of conventional mesophilic SRB (origin: paper waste water treatment plant Parenco, NL and mining waste water treatment plant Budelco, NL). The reactor was supplied with sulphite, 2500 mg/l ($\approx$3940 mg $Na_2SO_3$/l) and sulphate, 750 mg/l ($\approx$1110 mg $Na_2SO_4$/l), nutrient flow 1800 ml/h and with hydrogen, 6000 ml/h, as the electron donor. The sulphide concentration was never higher than 500 mg $S^{2-}$/l. The reactor was run for one year, so the sludge was adapted to high temperature.

After inoculation with KT7, 250 ml, the sulphide concentration increased to 600/700 mg $S^{2-}$/l in 1 week and to 800–1000 mg $S^{2-}$/l in 7 weeks. No more sulphide could be formed because of the composition of the influent. Physiological and morphological analysis of bacterial samples showed that the strain responsible for the higher sulphide concentration was the KT7 strain.

Example 2

A reactor of 6.5 l was run under anaerobic conditions at 50° C., pH 7.0.and conductivity of 20–25 mS/cm. The reactor was supplied with sulphite/sulphate as in Example 1. Nutrient flow was up to 300 ml/h and hydrogen flow was up to 1300 ml/h. Acetate (100 mg/l) and yeast (1 mg/l) were present as organic carbon sources. The reactor was inoculated with KT7 (0.54 g) from the start, without other sludge.

After some days, the sulphide concentration reached 800–1000 mg/l; no more sulphide could be formed because of the composition of the influent. After this, the acetate and yeast were left out of the medium (supply discontinued). After another 2–3 weeks the sulphide concentration again reached 800–1000 mg/l.

Example 3

Example 2 was repeated, with the exception that the reactor did not contain any acetate or yeast. Some weeks after inoculation with KT7, the sulphide concentration reached 800–1000 mg/l.

Example 4

In a pilot desulphurisation plant at the Power Station of Geertruidenberg (NL), the anaerobic, hydrogen-fed reactor had a volume of 5.5 $m^3$, pH 7–7.5, conductivity 10–30 mS/cm. Four kg of $SO_2$ per h was absorbed in the gas scrubber and fed to the anaerobic reactor in the form of sulphite and sulphate. The reactor was operated at 50° C. The reactor was started with a mixture of bacteria, largely conventional SRB (gas desulphurisation and paper waste treatment) and partly KT7 bacteria (<1%).

The sulphide concentration reached 1500 mg $S^{2-}$/l after two weeks. The sulphide production reached a level of 15 kg/$m^3$.day. After six months, KT7 was still dominant in the reactor.

What is claimed is:

1. Sulfur-reducing bacterium, being a low-GC Gram-positive bacterium related to the genus Desulfotomaculum, capable of reducing sulfite and/or sulfate to sulfide, growing at a temperature between 35 and 85° C., at a pH of between 5 and 9, at a conductivity of 0–40 mS/cm, and tolerating sulfide concentrations of up to 2.5 g/l.

2. The sulfur-reducing bacterium according to claim 1, as deposited at the DSMZ with accession number DSM 11017.

3. Process for the removal of sulfur compounds from water, which comprises: subjecting the water to an anaerobic treatment with sulfur-reducing bacteria, in the presence of an electron donor to reduce sulfite and/or sulfate to sulfide, said sulfur-reducing bacteria comprising a low-GC Gram-positive bacterium related to the genus Desulfotomaculum, growing at a temperature between 35 and 85° C., at a pH of between 5 and 9, at a conductivity of 0–40 mS/cm, and tolerating sulfide concentrations of up to 2.5 g/l.

4. The process according to claim 3, wherein a sulfide concentration above 500 mg/l is maintained during the anaerobic treatment.

5. The process according to claim 3, wherein the electron donor is hydrogen.

6. The process according to claim 3, wherein the anaerobic treatment is carried out at a temperature of 45–70° C.

7. The process according to claim 3, wherein the sulfur compounds are selected from the group consisting of sulfite, sulfate, and thiosulfate.

8. The process according to claim 3, wherein sulfide formed is oxidized to elemental sulfur and the sulfur formed is removed.

9. The process according to claim 3, wherein the sulfur compounds are contained in a wash liquid originating from washing a flue gas, and said treatment results in regeneration of the wash liquid.

10. The process according to claim 3, wherein the sulfur compounds are contained in a wash liquid originating from washing a flue gas, and said treatment results in regeneration of the wash liquid, and the sulfide formed is oxidized in an oxidation step to elemental sulfur, and the sulfur formed is removed.

11. The process according to claim 10, wherein a part of the liquid obtained by oxidation of the sulfide is subjected to a second anaerobic treatment, and is subsequently returned to the oxidation step.

12. The process according to claim 3, wherein said sulfur-reducing bacteria comprise a sulfur-reducing bacterium, as deposited at the DSMZ with accession number DSM 11017.

* * * * *